US011319350B2

(12) United States Patent
Blackledge et al.

(10) Patent No.: US 11,319,350 B2
(45) Date of Patent: May 3, 2022

(54) METHOD FOR PRODUCING SELF-ASSEMBLING PARAMYXOVIRAL NUCLEOCAPSID-LIKE PARTICLES AND THEIR USES

(71) Applicants: COMMISSARIAT A L'ENERGIE ATOMIQUE ET AUX ENERGIES ALTERNATIVES, Paris (FR); UNIVERSITE GRENOBLE ALPES, Saint-Martin-d'Hères (FR)

(72) Inventors: Martin Blackledge, Grenoble (FR); Marlène Ringkjobing-Jensen, Grenoble (FR); Sigrid Milles, Grenoble (FR); Robertus Ruigrok, Grenoble (FR); Guy Schoehn, Grenoble (FR); Guillaume Communie, Grenoble (FR)

(73) Assignees: Centre National De La Recherche Scientifique, Paris (FR); Universite Grenoble Alpes, Saint-Martin-D'Heres (FR); Commissariat A L'Energie Atomique Et Aux Energies Alternatives, Paris (FR)

( * ) Notice: Subject to any disclaimer, the term of this patent is extended or adjusted under 35 U.S.C. 154(b) by 0 days.

(21) Appl. No.: 16/306,843

(22) PCT Filed: Jun. 6, 2017

(86) PCT No.: PCT/EP2017/063735
§ 371 (c)(1),
(2) Date: Dec. 3, 2018

(87) PCT Pub. No.: WO2017/211846
PCT Pub. Date: Dec. 14, 2017

(65) Prior Publication Data
US 2019/0292229 A1 Sep. 26, 2019

(30) Foreign Application Priority Data
Jun. 6, 2016 (EP) .................................. 16305658

(51) Int. Cl.
*C07K 14/11* (2006.01)
*C07K 14/005* (2006.01)
*G01N 33/569* (2006.01)
*C12N 7/00* (2006.01)

(52) U.S. Cl.
CPC .............. *C07K 14/005* (2013.01); *C12N 7/00* (2013.01); *G01N 33/56983* (2013.01); *C07K 2319/00* (2013.01); *C12N 2760/18423* (2013.01); *C12N 2760/18433* (2013.01); *C12N 2760/18434* (2013.01); *C12N 2760/18451* (2013.01)

(58) Field of Classification Search
CPC ............. C07K 14/005; G01N 33/6812; G01N 2405/04; G01N 2333/165; G01N 2800/50; G01N 33/56983; G01N 15/10; G01N 15/1475; G01N 1/2806; G01N 2015/0038; C12Q 1/70; A61B 5/00; C12N 2750/14121; C12N 2750/14123; C12N 2760/18723; C12N 2760/18423; C12N 2760/18462; C12N 2760/18523; C12N 2760/18571; C12N 2760/18823; C12N 2760/18834; C12N 2770/36143; C12N 5/0012; A61K 39/155; A61K 2039/5258
See application file for complete search history.

(56) References Cited

U.S. PATENT DOCUMENTS

| 7,951,384 | B2 * | 5/2011 | Morrison | ............... A61K 39/17 424/214.1 |
| 8,586,364 | B2 * | 11/2013 | Tangy | .................. C07K 14/005 435/455 |
| 2010/0021490 | A1 | 1/2010 | Eleouet et al. | |

FOREIGN PATENT DOCUMENTS

| WO | 2006/117456 A1 | 11/2006 |
| WO | 2016/009044 A1 | 1/2016 |

OTHER PUBLICATIONS

Horikami et al. Journal of Virology, 1992, vol. 66, No. 8, pp. 4901-4908.*
Spehner et al. Virology, 1997, vol. 232, pp. 262-268.*
Guyanov et al. Journal of Virology, published on line on Feb. 2016, vol. 90, (6), pp. 2849-2857.*
International Search Report dated Sep. 21, 2017, issued in corresponding International Application No. PCT/EP2017/063735, filed Jun. 6, 2017, 5 pages.
Written Opinion of the International Searching Authority dated Sep. 21, 2017, issued in corresponding International Application No. PCT/EP2017/063735, filed Jun. 6, 2017, 8 pages.
Spehner, D., et al., "The Assembly of the Measles Virus Nucleoprotein into Nucleocapsid-like Particles Is Modulated by the Phosphoprotein," Virology 232(2):260-268, Jun. 1997.
Moore, P.M.E., et al., "Measles Virus Nucleocapsids: Large-Scale Purification and Use in Radioimmunoassays," Infection and Immunity American Society for Microbiology 20(3):842-846, Jun. 1978.

(Continued)

*Primary Examiner* — Bao Q Li
(74) *Attorney, Agent, or Firm* — Christensen O'Connor Johnson Kindness PLLC

(57) ABSTRACT

Embodiments of the disclosure relate to the domain of virology of Paramyxoviruses. The disclosure concerns a method for producing self-assembling paramyxoviral particles and a method for identifying a compound able to inhibit the replication or the transcription of a Paramyxovirus. The disclosure also pertains to the nucleocapsid-like particles obtainable by the method of the invention and their use for biotechnological and pharmaceutical applications.

7 Claims, 7 Drawing Sheets
Specification includes a Sequence Listing.

(56) References Cited

OTHER PUBLICATIONS

Guryanov, S.G., et al., "Crystal Structure of the Measles Virus Nucleoprotein Core in Complex with an N-Terminal Region of Phosphoprotein," Journal of Virology 90(6):2849-2857, Mar. 2016.

Renner, M., et al., "Nucleocapsid assembly in pneumoviruses is regulated by conformational switching of the N protein," ELIFE 5:e12627, Feb. 2016.

Yabukarski, F., et al., "Structure of Nipah virus unassembled nucleoprotein in complex with its viral chaperone," Nature Structural & Molecular Biology 21(9):754-759, Sep. 2014.

Cox, R., et al., "Characterization of a Mumps Virus Nucleocapsid-like Particle," Journal of Virology 83(21):11402-11406, Nov. 2009.

Juozapaitis, M., et al., "Generation of Sendai virus nucleocapsid-like particles in yeast," Virus Research 108(1-2):221-224, Mar. 2005.

Petraityte-Burneikiene, R., et al., "Generation of recombinant metapneumovirus nucleocapsid protein as nucleocapsid-like particles and development of virus-specific monoclonal antibodies," Virus Research 161(2):131-139, Jul. 2011.

Chapman, J., et al., "RSV604, a Novel Inhibitor of Respiratory Syncytial Virus Replication," Antimicrobial Agents and Chemotherapy 51(9):3346-3353, Sep. 2007.

Milles, S., et al., "Self-Assembly of Measles Virus Nucleocapsid-like Particles: Kinetics and RNA Sequence Dependence," 55(32):9356-9360, Jun. 2016.

* cited by examiner

SEQUENCE LISTING

```
<160> NUMBER OF SEQ ID NOS: 20

<210> SEQ ID NO 1
<211> LENGTH: 507
<212> TYPE: PRT
<213> ORGANISM: Measles virus

<400> SEQUENCE: 1

Met Ala Glu Glu Gln Ala Arg His Val Lys Asn Gly Leu Glu Cys Ile
1               5                   10                  15

Arg Ala Leu Lys Ala Glu Pro Ile Gly Ser Leu Ala Ile Glu Glu Ala
            20                  25                  30

Met Ala Ala Trp Ser Glu Ile Ser Asp Asn Pro Gly Gln Glu Arg Ala
        35                  40                  45

Thr Cys Arg Glu Glu Lys Ala Gly Ser Ser Gly Leu Ser Lys Pro Cys
50                  55                  60

Leu Ser Ala Ile Gly Ser Thr Glu Gly Gly Ala Pro Arg Ile Arg Gly
65                  70                  75                  80

Gln Gly Pro Gly Glu Ser Asp Asp Asp Ala Glu Thr Leu Gly Ile Pro
                85                  90                  95

Pro Arg Asn Leu Gln Ala Ser Ser Thr Gly Leu Gln Cys His Tyr Val
            100                 105                 110

Tyr Asp His Ser Gly Glu Ala Val Lys Gly Ile Gln Asp Ala Asp Ser
        115                 120                 125

Ile Met Val Gln Ser Gly Leu Asp Gly Asp Ser Thr Leu Ser Gly Gly
130                 135                 140

Asp Asn Glu Ser Glu Asn Ser Asp Val Asp Ile Gly Glu Pro Asp Thr
145                 150                 155                 160

Glu Gly Tyr Ala Ile Thr Asp Arg Gly Ser Ala Pro Ile Ser Met Gly
                165                 170                 175

Phe Arg Ala Ser Asp Val Glu Thr Ala Glu Gly Gly Glu Ile His Glu
            180                 185                 190

Leu Leu Arg Leu Gln Ser Arg Gly Asn Asn Phe Pro Lys Leu Gly Lys
        195                 200                 205

Thr Leu Asn Val Pro Pro Pro Asp Pro Gly Arg Ala Ser Thr Ser
210                 215                 220

Gly Thr Pro Ile Lys Lys Gly Thr Asp Ala Arg Leu Ala Ser Phe Gly
225                 230                 235                 240

Thr Glu Ile Ala Ser Ser Leu Thr Gly Gly Ala Thr Gln Cys Ala Arg
                245                 250                 255

Lys Ser Pro Ser Glu Pro Ser Gly Pro Gly Ala Pro Ala Gly Asn Val
            260                 265                 270

Pro Glu Cys Val Ser Asn Ala Ala Leu Ile Gln Glu Trp Thr Pro Glu
        275                 280                 285

Ser Gly Thr Thr Ile Ser Pro Arg Ser Gln Asn Asn Glu Glu Gly Gly
    290                 295                 300

Asp His Tyr Asp Asp Glu Leu Phe Ser Asp Val Gln Asp Ile Lys Thr
305                 310                 315                 320
```

```
Ala Leu Ala Lys Ile His Glu Asp Asn Gln Lys Ile Ile Ser Lys Leu
                325                 330                 335

Glu Ser Leu Leu Leu Lys Gly Glu Val Glu Ser Ile Lys Lys Gln
        340                 345                 350

Ile Asn Arg Gln Asn Ile Ser Ile Ser Thr Leu Glu Gly His Leu Ser
            355                 360                 365

Ser Ile Met Ile Ala Ile Pro Gly Leu Gly Lys Asp Pro Asn Asp Pro
    370                 375                 380

Thr Ala Asp Val Glu Ile Asn Pro Asp Leu Lys Pro Ile Ile Gly Arg
385                 390                 395                 400

Asp Ser Gly Arg Ala Leu Ala Glu Val Leu Lys Lys Pro Val Ala Ser
                405                 410                 415

Arg Gln Leu Gln Gly Met Thr Asn Gly Arg Thr Ser Ser Arg Gly Gln
            420                 425                 430

Leu Leu Lys Glu Phe Gln Leu Lys Pro Ile Gly Lys Lys Met Ser Ser
        435                 440                 445

Ala Val Gly Phe Val Pro Asp Thr Gly Pro Ala Ser Arg Ser Val Ile
    450                 455                 460

Arg Ser Ile Ile Lys Ser Ser Arg Leu Glu Glu Asp Arg Lys Arg Tyr
465                 470                 475                 480

Leu Met Thr Leu Leu Asp Asp Ile Lys Gly Ala Asn Asp Leu Ala Lys
                485                 490                 495

Phe His Gln Met Leu Met Lys Ile Ile Met Lys
                500                 505

<210> SEQ ID NO 2
<211> LENGTH: 50
<212> TYPE: PRT
<213> ORGANISM: Measles virus

<400> SEQUENCE: 2

Met Ala Glu Glu Gln Ala Arg His Val Lys Asn Gly Leu Glu Cys Ile
1               5                   10                  15

Arg Ala Leu Lys Ala Glu Pro Ile Gly Ser Leu Ala Ile Glu Glu Ala
            20                  25                  30

Met Ala Ala Trp Ser Glu Ile Ser Asp Asn Pro Gly Gln Glu Arg Ala
        35                  40                  45

Thr Cys
    50

<210> SEQ ID NO 3
<211> LENGTH: 57
<212> TYPE: PRT
<213> ORGANISM: artificial
<220> FEATURE:
<223> OTHER INFORMATION: Measles virus P with TEV cleavage peptide

<400> SEQUENCE: 3

Met Ala Glu Glu Gln Ala Arg His Val Lys Asn Gly Leu Glu Cys Ile
1               5                   10                  15

Arg Ala Leu Lys Ala Glu Pro Ile Gly Ser Leu Ala Ile Glu Glu Ala
            20                  25                  30

Met Ala Ala Trp Ser Glu Ile Ser Asp Asn Pro Gly Gln Glu Arg Ala
        35                  40                  45

Thr Cys Glu Asn Leu Tyr Phe Gln Asn
    50                  55
```

<210> SEQ ID NO 4
<211> LENGTH: 525
<212> TYPE: PRT
<213> ORGANISM: Measles virus

<400> SEQUENCE: 4

Met Ala Thr Leu Leu Arg

-continued

Gly Ile Thr Ala Glu Asp Ala Arg Leu Val Ser Glu Ile Ala Met His
385                 390                 395                 400

Thr Thr Glu Asp Arg Thr Ser Arg Ala Val Gly Pro Arg Gln Ala Gln
            405                 410                 415

Val Ser Phe Leu His Gly Asp Gln Ser Glu Asn Glu Leu Pro Gly Leu
        420                 425                 430

Gly Gly Lys Glu Asp Arg Arg Val Arg Gln Ser Arg Gly Glu Ala Arg
        435                 440                 445

Glu Ser Asn Arg Glu Ile Gly Ser Ser Arg Leu Ser Asp Ala Arg Ala
    450                 455                 460

Ala His Leu Pro Thr Ser Thr Pro Leu Asp Ile Asp Thr Ala Ser Glu
465                 470                 475                 480

Ser Gly Gln Asp Pro Gln Asp Ser Arg Arg Ser Ala Asp Ala Leu Leu
            485                 490                 495

Arg Leu Gln Ala Met Ala Gly Ile Leu Glu Glu Gln Gly Ser Asp Thr
        500                 505                 510

Asp Thr Pro Arg Val Tyr Asn Asp Arg Asp Leu Leu Asp
        515                 520                 525

<210> SEQ ID NO 5
<211> LENGTH: 405
<212> TYPE: PRT
<213> ORGANISM: Measles virus

<400> SEQUENCE: 5

Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Gln Tyr Phe Ser His Asp Asp Pro Ser Ser Ser Asp Gln Ser Arg Ser
    130                 135                 140

Gly Trp Phe Glu Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
    210                 215                 220

Glu Asp Leu Ser Leu Arg Arg Phe Met Val Ala Leu Ile Leu Asp Ile
225                 230                 235                 240

-continued

```
Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Arg
                405

<210> SEQ ID NO 6
<211> LENGTH: 536
<212> TYPE: PRT
<213> ORGANISM: artificial
<220> FEATURE:
<223> OTHER INFORMATION: Measles virus N with His tag

<400> SEQUENCE: 6

Gly Met Ala Thr Leu Leu Arg Ser Leu Ala Leu Phe Lys Arg Asn Lys
1               5                   10                  15

Asp Lys Pro Pro Ile Thr Ser Gly Ser Gly Gly Ala Ile Arg Gly Ile
            20                  25                  30

Lys His Ile Ile Ile Val Pro Ile Pro Gly Asp Ser Ser Ile Thr Thr
        35                  40                  45

Arg Ser Arg Leu Leu Asp Arg Leu Val Arg Leu Ile Gly Asn Pro Asp
    50                  55                  60

Val Ser Gly Pro Lys Leu Thr Gly Ala Leu Ile Gly Ile Leu Ser Leu
65                  70                  75                  80

Phe Val Glu Ser Pro Gly Gln Leu Ile Gln Arg Ile Thr Asp Asp Pro
                85                  90                  95

Asp Val Ser Ile Arg Leu Leu Glu Val Val Gln Ser Asp Gln Ser Gln
            100                 105                 110

Ser Gly Leu Thr Phe Ala Ser Arg Gly Thr Asn Met Glu Asp Glu Ala
        115                 120                 125

Asp Gln Tyr Phe Ser His Asp Asp Pro Ile Ser Ser Asp Gln Ser Arg
    130                 135                 140

Phe Gly Trp Phe Glu Asn Lys Glu Ile Ser Asp Ile Glu Val Gln Asp
145                 150                 155                 160

Pro Glu Gly Phe Asn Met Ile Leu Gly Thr Ile Leu Ala Gln Ile Trp
                165                 170                 175
```

-continued

Val Leu Leu Ala Lys Ala Val Thr Ala Pro Asp Thr Ala Ala Asp Ser
            180                 185                 190

Glu Leu Arg Arg Trp Ile Lys Tyr Thr Gln Gln Arg Val Val Gly
            195                 200                 205

Glu Phe Arg Leu Glu Arg Lys Trp Leu Asp Val Val Arg Asn Arg Ile
210                 215                 220

Ala Glu Asp Leu Ser Leu Arg Arg Phe Met Val Ala Leu Ile Leu Asp
225                 230                 235                 240

Ile Lys Arg Thr Pro Gly Asn Lys Pro Arg Ile Ala Glu Met Ile Cys
            245                 250                 255

Asp Ile Asp Thr Tyr Ile Val Glu Ala Gly Leu Ala Ser Phe Ile Leu
            260                 265                 270

Thr Ile Lys Phe Gly Ile Glu Thr Met Tyr Pro Ala Leu Gly Leu His
            275                 280                 285

Glu Phe Ala Gly Glu Leu Ser Thr Leu Glu Ser Leu Met Asn Leu Tyr
            290                 295                 300

Gln Gln Met Gly Glu Thr Ala Pro Tyr Met Val Ile Leu Glu Asn Ser
305                 310                 315                 320

Ile Gln Asn Lys Phe Ser Ala Gly Ser Tyr Pro Leu Leu Trp Ser Tyr
            325                 330                 335

Ala Met Gly Val Gly Val Glu Leu Glu Asn Ser Met Gly Gly Leu Asn
            340                 345                 350

Phe Gly Arg Ser Tyr Phe Asp Pro Ala Tyr Phe Arg Leu Gly Gln Glu
            355                 360                 365

Met Val Arg Arg Ser Ala Gly Lys Val Ser Ser Thr Leu Ala Ser Glu
370                 375                 380

Leu Gly Ile Thr Ala Glu Asp Ala Arg Leu Val Ser Glu Ile Ala Met
385                 390                 395                 400

His Thr Thr Glu Asp Lys Ile Ser Arg Ala Val Gly Pro Arg Gln Ala
            405                 410                 415

Gln Val Ser Phe Leu His Gly Asp Gln Ser Glu Asn Glu Leu Pro Arg
            420                 425                 430

Leu Gly Gly Lys Glu Asp Arg Arg Val Lys Gln Ser Arg Gly Glu Ala
            435                 440                 445

Arg Glu Ser Tyr Arg Glu Thr Gly Pro Ser Arg Ala Ser Asp Ala Arg
450                 455                 460

Ala Ala His Leu Pro Thr Gly Thr Pro Leu Asp Ile Asp Thr Ala Ser
465                 470                 475                 480

Glu Ser Ser Gln Asp Pro Gln Asp Ser Arg Arg Ser Ala Asp Ala Leu
            485                 490                 495

Leu Arg Leu Gln Ala Met Ala Gly Ile Ser Glu Glu Gln Gly Ser Asp
            500                 505                 510

Thr Asp Thr Pro Ile Val Tyr Asn Asp Arg Asn Leu Leu Asp Val Glu
            515                 520                 525

His His His His His His His
    530                 535

<210> SEQ ID NO 7
<211> LENGTH: 416
<212> TYPE: PRT
<213> ORGANISM: artificial
<220> FEATURE:
<223> OTHER INFORMATION: Measles virus N folded domain with His tag

<400> SEQUENCE: 7

```
Gly Met Ala Thr Leu Leu Arg Ser Leu Ala Leu Phe Lys Arg Asn Lys
1               5                   10                  15

Asp Lys Pro Pro Ile Thr Ser Gly Gly Ala Ile Arg Gly Ile
            20                  25                  30

Lys His Ile Ile Ile Val Pro Ile Pro Gly Asp Ser Ile Thr Thr
                35                  40                  45

Arg Ser Arg Leu Leu Asp Arg Leu Val Arg Leu Ile Gly Asn Pro Asp
        50                  55                  60

Val Ser Gly Pro Lys Leu Thr Gly Ala Leu Ile Gly Ile Leu Ser Leu
65                  70                  75                  80

Phe Val Glu Ser Pro Gly Gln Leu Ile Gln Arg Ile Thr Asp Asp Pro
                85                  90                  95

Asp Val Ser Ile Arg Leu Leu Glu Val Val Gln Ser Asp Gln Ser Gln
                100                 105                 110

Ser Gly Leu Thr Phe Ala Ser Arg Gly Thr Asn Met Glu Asp Glu Ala
            115                 120                 125

Asp Gln Tyr Phe Ser His Asp Pro Ile Ser Ser Asp Gln Ser Arg
        130                 135                 140

Phe Gly Trp Phe Glu Asn Lys Glu Ile Ser Asp Ile Glu Val Gln Asp
145                 150                 155                 160

Pro Glu Gly Phe Asn Met Ile Leu Gly Thr Ile Leu Ala Gln Ile Trp
                165                 170                 175

Val Leu Leu Ala Lys Ala Val Thr Ala Pro Asp Thr Ala Ala Asp Ser
            180                 185                 190

Glu Leu Arg Arg Trp Ile Lys Tyr Thr Gln Gln Arg Val Val Gly
            195                 200                 205

Glu Phe Arg Leu Glu Arg Lys Trp Leu Asp Val Val Arg Asn Arg Ile
            210                 215                 220

Ala Glu Asp Leu Ser Leu Arg Arg Phe Met Val Ala Leu Ile Leu Asp
225                 230                 235                 240

Ile Lys Arg Thr Pro Gly Asn Lys Pro Arg Ile Ala Glu Met Ile Cys
                245                 250                 255

Asp Ile Asp Thr Tyr Ile Val Glu Ala Gly Leu Ala Ser Phe Ile Leu
            260                 265                 270

Thr Ile Lys Phe Gly Ile Glu Thr Met Tyr Pro Ala Leu Gly Leu His
        275                 280                 285

Glu Phe Ala Gly Glu Leu Ser Thr Leu Glu Ser Leu Met Asn Leu Tyr
        290                 295                 300

Gln Gln Met Gly Glu Thr Ala Pro Tyr Met Val Ile Leu Glu Asn Ser
305                 310                 315                 320

Ile Gln Asn Lys Phe Ser Ala Gly Ser Tyr Pro Leu Leu Trp Ser Tyr
            325                 330                 335

Ala Met Gly Val Gly Val Glu Leu Glu Asn Ser Met Gly Gly Leu Asn
            340                 345                 350

Phe Gly Arg Ser Tyr Phe Asp Pro Ala Tyr Phe Arg Leu Gly Gln Glu
        355                 360                 365

Met Val Arg Arg Ser Ala Gly Lys Val Ser Ser Thr Leu Ala Ser Glu
        370                 375                 380

Leu Gly Ile Thr Ala Glu Asp Ala Arg Leu Val Ser Glu Ile Ala Met
385                 390                 395                 400

His Thr Thr Glu Asp Lys Val Glu His His His His His His
        405                 410                 415
```

<210> SEQ ID NO 8
<211> LENGTH: 60
<212> TYPE: RNA
<213> ORGANISM: Measles virus

<400> SEQUENCE: 8
accagacaaa gcugggaaua gaaacuucgu auuuucaaag uuuucuuuaa uauauugcaa 60

<210> SEQ ID NO 9
<211> LENGTH: 38
<212> TYPE: DNA
<213> ORGANISM: artificial
<220> FEATURE:
<223> OTHER INFORMATION: primer

<400> SEQUENCE: 9
ggaattccat atggcagagg agcaggcacg ccatgtca 38

<210> SEQ ID NO 10
<211> LENGTH: 40
<212> TYPE: DNA
<213> ORGANISM: artificial
<220> FEATURE:
<223> OTHER INFORMATION: primer

<400> SEQUENCE: 10
catgccctga aaatacaggt tttcgcaggt ggctcgctcc 40

<210> SEQ ID NO 11
<211> LENGTH: 47
<212> TYPE: DNA
<213> ORGANISM: artificial
<220> FEATURE:
<223> OTHER INFORMATION: primer

<400> SEQUENCE: 11
gccacctgcg aaaacctgta ttttcagggc atggccacac ttttaag 47

<210> SEQ ID NO 12
<211> LENGTH: 46
<212> TYPE: DNA
<213> ORGANISM: artificial
<220> FEATURE:
<223> OTHER INFORMATION: primer

<400> SEQUENCE: 12
ccggtcgacg tctagaagat ttctgtcatt gtacactata ggggtg 46

<210> SEQ ID NO 13
<211> LENGTH: 40
<212> TYPE: DNA
<213> ORGANISM: artificial
<220> FEATURE:
<223> OTHER INFORMATION: primer

<400> SEQUENCE: 13
gcgtcgacct tgtcctcagt agtatgcatt gcaatctctg 40

<210> SEQ ID NO 14
<211> LENGTH: 10
<212> TYPE: RNA
<213> ORGANISM: Measles virus

<400> SEQUENCE: 14
accagacaaa 10

<210> SEQ ID NO 15
<211> LENGTH: 532
<212> TYPE: PRT
<213> ORGANISM: Nipah virus

<400> SEQUENCE: 15

```
Met Ser Asp Ile Phe Glu Glu Ala Ala Ser Phe Arg Ser Tyr Gln Ser
1               5                   10                  15

Lys Leu Gly Arg Asp Gly Arg Ala Ser Ala Ala Thr Ala Thr Leu Thr
            20                  25                  30

Thr Lys Ile Arg Ile Phe Val Pro Ala Thr Asn Ser Pro Glu Leu Arg
        35                  40                  45

Trp Glu Leu Thr Leu Phe Ala Leu Asp Val Ile Arg Ser Pro Ser Ala
    50                  55                  60

Ala Glu Ser Met Lys Val Gly Ala Ala Phe Thr Leu Ile Ser Met Tyr
65                  70                  75                  80

Ser Glu Arg Pro Gly Ala Leu Ile Arg Ser Leu Leu Asn Asp Pro Asp
                85                  90                  95

Ile Glu Ala Val Ile Ile Asp Val Gly Ser Met Val Asn Gly Ile Pro
            100                 105                 110

Val Met Glu Arg Arg Gly Asp Lys Ala Gln Glu Glu Met Glu Gly Leu
        115                 120                 125

Met Arg Ile Leu Lys Thr Ala Arg Asp Ser Ser Lys Gly Lys Thr Pro
130                 135                 140

Phe Val Asp Ser Arg Ala Tyr Gly Leu Arg Ile Thr Asp Met Ser Thr
145                 150                 155                 160

Leu Val Ser Ala Val Ile Thr Ile Glu Ala Gln Ile Trp Ile Leu Ile
                165                 170                 175

Ala Lys Ala Val Thr Ala Pro Asp Thr Ala Glu Glu Ser Glu Thr Arg
            180                 185                 190

Arg Trp Ala Lys Tyr Val Gln Gln Lys Arg Val Asn Pro Phe Phe Ala
        195                 200                 205

Leu Thr Gln Gln Trp Leu Thr Glu Met Arg Asn Leu Leu Ser Gln Ser
    210                 215                 220

Leu Ser Val Arg Lys Phe Met Val Glu Ile Leu Ile Glu Val Lys Lys
225                 230                 235                 240

Gly Gly Ser Ala Lys Gly Arg Ala Val Glu Ile Ile Ser Asp Ile Gly
                245                 250                 255

Asn Tyr Val Glu Glu Thr Gly Met Ala Gly Phe Phe Ala Thr Ile Arg
            260                 265                 270

Phe Gly Leu Glu Thr Arg Tyr Pro Ala Leu Ala Leu Asn Glu Phe Gln
        275                 280                 285

Ser Asp Leu Asn Thr Ile Lys Ser Leu Met Leu Leu Tyr Arg Glu Ile
    290                 295                 300

Gly Pro Arg Ala Pro Tyr Met Val Leu Leu Glu Glu Ser Ile Gln Thr
305                 310                 315                 320

Lys Phe Ala Pro Gly Gly Tyr Pro Leu Leu Trp Ser Phe Ala Met Gly
                325                 330                 335

Val Ala Thr Thr Ile Asp Arg Ser Met Gly Ala Leu Asn Ile Asn Arg
            340                 345                 350

Gly Tyr Leu Glu Pro Met Tyr Phe Arg Leu Gly Gln Lys Ser Ala Arg
        355                 360                 365

His His Ala Gly Gly Ile Asp Gln Asn Met Ala Asn Arg Leu Gly Leu
    370                 375                 380
```

```
Ser Ser Asp Gln Val Ala Glu Leu Ala Ala Ala Val Gln Glu Thr Ser
385                 390                 395                 400

Ala Gly Arg Gln Glu Ser Asn Val Gln Ala Arg Glu Ala Lys Phe Ala
            405                 410                 415

Ala Gly Gly Val Leu Ile Gly Gly Ser Asp Gln Asp Ile Asp Glu Gly
            420                 425                 430

Glu Glu Pro Ile Glu Gln Ser Gly Arg Gln Ser Val Thr Phe Lys Arg
            435                 440                 445

Glu Met Ser Ile Ser Ser Leu Ala Asn Ser Val Pro Ser Ser Ser Val
    450                 455                 460

Ser Thr Ser Gly Gly Thr Arg Leu Thr Asn Ser Leu Leu Asn Leu Arg
465                 470                 475                 480

Ser Arg Leu Ala Ala Lys Ala Ala Lys Glu Ala Ala Ser Ser Asn Ala
            485                 490                 495

Thr Asp Asp Pro Ala Ile Ser Asn Arg Thr Gln Gly Glu Ser Glu Lys
            500                 505                 510

Lys Asn Asn Gln Asp Leu Lys Pro Ala Gln Asn Asp Leu Asp Phe Val
            515                 520                 525

Arg Ala Asp Val
    530

<210> SEQ ID NO 16
<211> LENGTH: 709
<212> TYPE: PRT
<213> ORGANISM: Nipah virus

<400> SEQUENCE: 16

Met Asp Lys Leu Glu Leu Val Asn Asp Gly Leu Asn Ile Ile Asp Phe
1               5                   10                  15

Ile Gln Lys Asn Gln Lys Glu Ile Gln Lys Thr Tyr Gly Arg Ser Ser
            20                  25                  30

Ile Gln Gln Pro Ser Ile Lys Asp Gln Thr Lys Ala Trp Glu Asp Phe
        35                  40                  45

Leu Gln Cys Thr Ser Gly Glu Ser Glu Gln Val Glu Gly Gly Met Ser
    50                  55                  60

Lys Asp Asp Gly Asp Val Glu Arg Arg Asn Leu Glu Asp Leu Ser Ser
65                  70                  75                  80

Thr Ser Pro Thr Asp Gly Thr Ile Gly Lys Arg Val Ser Asn Thr Arg
                85                  90                  95

Asp Trp Ala Glu Gly Ser Asp Asp Ile Gln Leu Asp Pro Val Val Thr
            100                 105                 110

Asp Val Val Tyr His Asp His Gly Gly Glu Cys Thr Gly Tyr Gly Phe
            115                 120                 125

Thr Ser Ser Pro Glu Arg Gly Trp Ser Asp Tyr Thr Ser Gly Ala Asn
    130                 135                 140

Asn Gly Asn Val Cys Leu Val Ser Asp Ala Lys Met Leu Ser Tyr Ala
145                 150                 155                 160

Pro Glu Ile Ala Val Ser Lys Glu Asp Arg Glu Thr Asp Leu Val His
                165                 170                 175

Leu Glu Asn Lys Leu Ser Thr Thr Gly Leu Asn Pro Thr Ala Val Pro
            180                 185                 190

Phe Thr Leu Arg Asn Leu Ser Asp Pro Ala Lys Asp Ser Pro Val Ile
        195                 200                 205

Ala Glu His Tyr Tyr Gly Leu Gly Val Lys Glu Gln Asn Val Gly Pro
    210                 215                 220
```

-continued

```
Gln Thr Ser Arg Asn Val Asn Leu Asp Ser Ile Lys Leu Tyr Thr Ser
225                 230                 235                 240

Asp Asp Glu Glu Ala Asp Gln Leu Glu Phe Glu Asp Glu Phe Ala Gly
                245                 250                 255

Ser Ser Ser Glu Val Ile Val Gly Ile Ser Pro Glu Asp Glu Glu Pro
            260                 265                 270

Ser Ser Val Gly Gly Lys Pro Asn Glu Ser Ile Gly Arg Thr Ile Glu
        275                 280                 285

Gly Gln Ser Ile Arg Asp Asn Leu Gln Ala Lys Asp Asn Lys Ser Thr
    290                 295                 300

Asp Val Pro Gly Ala Gly Pro Lys Asp Ser Ala Val Lys Glu Glu Pro
305                 310                 315                 320

Pro Gln Lys Arg Leu Pro Met Leu Ala Glu Glu Phe Glu Cys Ser Gly
                325                 330                 335

Ser Glu Asp Pro Ile Ile Arg Glu Leu Leu Lys Glu Asn Ser Leu Ile
            340                 345                 350

Asn Cys Gln Gln Gly Lys Asp Ala Gln Pro Pro Tyr His Trp Ser Ile
        355                 360                 365

Glu Arg Ser Ile Ser Pro Asp Lys Thr Glu Ile Val Asn Gly Ala Val
    370                 375                 380

Gln Thr Ala Asp Arg Gln Arg Pro Gly Thr Pro Met Pro Lys Ser Arg
385                 390                 395                 400

Gly Ile Pro Ile Lys Lys Gly Thr Asp Ala Lys Tyr Pro Ser Ala Gly
                405                 410                 415

Thr Glu Asn Val Pro Gly Ser Lys Ser Gly Ala Thr Arg His Val Arg
            420                 425                 430

Gly Ser Pro Pro Tyr Gln Glu Gly Lys Ser Val Asn Ala Glu Asn Val
        435                 440                 445

Gln Leu Asn Ala Ser Thr Ala Val Lys Glu Thr Asp Lys Ser Glu Val
    450                 455                 460

Asn Pro Val Asp Asn Asp Ser Leu Asp Asp Lys Tyr Ile Met Pro
465                 470                 475                 480

Ser Asp Asp Phe Ser Asn Thr Phe Phe Pro His Asp Thr Asp Arg Leu
                485                 490                 495

Asn Tyr His Ala Asp His Leu Gly Asp Tyr Asp Leu Glu Thr Leu Cys
            500                 505                 510

Glu Glu Ser Val Leu Met Gly Val Ile Asn Ser Ile Lys Leu Ile Asn
        515                 520                 525

Leu Asp Met Arg Leu Asn His Ile Glu Glu Val Lys Glu Ile Pro
    530                 535                 540

Lys Ile Ile Asn Lys Leu Glu Ser Ile Asp Arg Val Leu Ala Lys Thr
545                 550                 555                 560

Asn Thr Ala Leu Ser Thr Ile Glu Gly His Leu Val Ser Met Met Ile
                565                 570                 575

Met Ile Pro Gly Lys Gly Lys Gly Glu Arg Lys Gly Lys Asn Asn Pro
            580                 585                 590

Glu Leu Lys Pro Val Ile Gly Arg Asp Ile Leu Glu Gln Gln Ser Leu
        595                 600                 605

Phe Ser Phe Asp Asn Val Lys Asn Phe Arg Asp Gly Ser Leu Thr Asn
    610                 615                 620
```

-continued

```
Glu Pro Tyr Gly Ala Ala Val Gln Leu Arg Glu Asp Leu Ile Leu Pro
625                 630                 635                 640

Glu Leu Asn Phe Glu Glu Thr Asn Ala Ser Gln Phe Val Pro Met Ala
            645                 650                 655

Asp Asp Ser Ser Arg Asp Val Ile Lys Thr Leu Ile Arg Thr His Ile
                660                 665                 670

Lys Asp Arg Glu Leu Arg Ser Glu Leu Ile Gly Tyr Leu Asn Lys Ala
            675                 680                 685

Glu Asn Asp Glu Glu Ile Gln Glu Ile Ala Asn Thr Val Asn Asp Ile
            690                 695                 700

Ile Asp Gly Asn Ile
705

<210> SEQ ID NO 17
<211> LENGTH: 50
<212> TYPE: PRT
<213> ORGANISM: Nipah virus

<400> SEQUENCE: 17

Met Asp Lys Leu Glu Leu Val Asn Asp Gly Leu Asn Ile Ile Asp Phe
1               5                   10                  15

Ile Gln Lys Asn Gln Lys Glu Ile Gln Lys Thr Tyr Gly Arg Ser Ser
                20                  25                  30

Ile Gln Gln Pro Ser Ile Lys Asp Gln Thr Lys Ala Trp Glu Asp Phe
            35                  40                  45

Leu Gln
    50

<210> SEQ ID NO 18
<211> LENGTH: 10
<212> TYPE: RNA
<213> ORGANISM: Measles virus

<400> SEQUENCE: 18
accagacaaa                                                              10

<210> SEQ ID NO 19
<211> LENGTH: 10
<212> TYPE: RNA
<213> ORGANISM: Artificial Sequence
<220> FEATURE:
<223> OTHER INFORMATION: Synthetic oligonucleotide

<400> SEQUENCE: 19
aaaaaaaaaa                                                              10

<210> SEQ ID NO 20
<211> LENGTH: 10
<212> TYPE: RNA
<213> ORGANISM: Artificial Sequence
<220> FEATURE:
<223> OTHER INFORMATION: Synthetic oligonucleotide

<400> SEQUENCE: 20
uuuuuuuuuu                                                              10
```

METHOD FOR PRODUCING SELF-ASSEMBLING PARAMYXOVIRAL NUCLEOCAPSID-LIKE PARTICLES AND THEIR USES

The invention pertains to the domain of virology of Paramyxoviruses. The invention concerns a method for producing self-assembling paramyxoviral particles and a method for identifying a compound able to inhibit the replication or the transcription of a Paramyxovirus. The invention also pertains to the nucleocapsid-like particles obtainable by the method of the invention and their use for biotechnological and pharmaceutical applications.

BACKGROUND

Paramyxoviridae comprise dangerous human pathogens, for example Measles, an important human pathogen that is responsible for 150000 deaths per year, but also Nipah and Hendra viruses, whose infection of humans has been exacerbated by urbanization of the natural hosts (fruitbats) due to the destruction of their natural habitats (deforestation). Paramyxoviruses, and the closely related filoviruses (including Ebola) therefore present an increasingly serious risk to human health. Paramyxoviruses are non-segmented negative strand RNA viruses that express their own machinery for transcription and replication. Paramyxoviral genomes are packaged into large helical nucleoprotein assemblies, termed nucleocapsids (NC), comprising a multitude of copies of the nucleoprotein (N) that bind the entire sequence of the viral genome[1]. The N-RNA complex provides the template for replication and transcription by the viral polymerase complex consisting of the large protein (L) carrying the enzymatic activity and its co-factor phosphoprotein (P). N is a two-domain protein, comprising an RNA binding domain ($N_{CORE}$), approximately 400 amino acids (aa), and a 125 aa intrinsically disordered C-terminal domain ($N_{TAIL}$)[2].

Paramyxoviral NCs have been studied in great detail using structural biology techniques such as electron microscopy[3-7], X-ray crystallography[8] and nuclear magnetic resonance spectroscopy[9,10] They are now understood quite well in terms of three-dimensional structure. While knowledge of the three dimensional structures can help in rational drug design, successful attempts to crystallize monomeric nucleoproteins of paramyxoviruses have required the cleavage of flexible regions of the protein[8], to enhance packing in a crystalline lattice. However, these constructs do not assemble into NCs.

NC-like assemblies have been purified from paramyxoviruses, or expressed in E. coli or insect cells[11-13]. These expressed particles do not specifically encapsulate a given RNA of interest but they assemble on cellular RNA. It has not yet been possible to reproduce the assembly process in vitro. The mechanism of assembly of NCs from these viral families remains one of the outstanding questions and potentially most exciting avenues for pharmaceutical intervention. The rational development of inhibitors of NC assembly is not possible if one cannot observe the process of assembly.

The inventors have now described an in vitro system wherein the self-assembling of the NC can be observed. They have designed new constructs of the so-called "N°P complex", a complex comprising elements from N and P, that can be solubilized in a heterodimeric form in vitro (FIG. 1), and subsequently used to assemble supramolecular NCs by controlled addition of RNA. Using these constructs, it is possible to detect and then follow the NC assembly process in real time using nuclear magnetic resonance (NMR) spectroscopy, fluorescence spectroscopy and electron microscopy. With this invention, the rational development of inhibitors of paramyxoviral NC assembly is now possible.

The present invention thus holds great promise for the development of targeted drugs against paramyxoviral diseases and also provides NC-like particles that could be useful in the development of vaccines.

DETAILED DESCRIPTION OF THE INVENTION

The present invention relates to the process of assembling NCs of Paramyxoviruses in vitro.

The inventors have successfully produced the N°P complex, a molecular association of N with a peptide derived from the P protein, in vitro. They have demonstrated that, provided that monomeric N is stabilized in an appropriate soluble form, NC-like particles can be assembled from recombinantly-expressed protein and RNA alone, in the absence of other viral or cellular partners.

Although NC-like particles from paramyxoviruses can be purified by over-expressing N in recombinant systems,[4] for example in E. coli, where N assembles on cellular RNA, the rational development of inhibitors of replication or transcription has been severely hampered by the inability to solubilize N°P and subsequently assemble supramolecular NC-like particles in vitro as multiple copies of N bind to the RNA.

The present invention relies on the demonstration that the 300 aa disordered N-terminal domain of P binds $N_{CORE}$, to chaperone monomeric RNA-free N prior to NC assembly on the RNA genome in the so-called N°P complex (FIG. 2). Crucially for this invention, monomeric N is insoluble in the absence of this chaperone. Further, the inventors have identified a minimal N-binding sequence of P.

A first object of the present invention consists of a method for producing self-assembling paramyxoviral NC-like particles.

The method for producing self-assembling paramyxoviral NC-like particles of the invention comprises the steps of:

(a) co-expressing recombinant N and P peptides in order to allow the formation of N°P complexes where the N peptide comprises at least the $N_{CORE}$ domain including the CTD arm and NTD arm, and the P peptide comprises at least the N-binding domain;

(b) adding RNA molecules to the N°P complex, wherein said RNA molecules comprise at least 6 nucleotides; and (c) recovering the resulting NC-like particles.

As demonstrated by the inventors, CTD arm and the NTD arm are required to interact with the neighboring N molecules within the NC and thus, the presence of the two arms of the $N_{CORE}$ protein is crucial for assembly of the N proteins into NC-like particles.

In an embodiment, the invention relates to the method for producing self-assembling paramyxoviral NC-like particles as described above, wherein the recombinant N peptide comprises the full-length nucleoprotein or at least the amino acids 1-405 corresponding to the $N_{CORE}$ domain of the nucleoprotein.

In particular, the recombinant N peptide is from 405 to 532 amino acids in length, preferably from 405 to 525 amino acids in length. For example, the recombinant N peptide comprises at least the $N_{CORE}$ domain of the nucleoprotein and has a length of 405, 410, 420, 430, 440, 450, 460, 470, 480, 490, 500, 510, 520, 525, 530 or 532 amino acids.

In an embodiment, the invention relates to the method for producing self-assembling paramyxoviral NC-like particles as described above, wherein the recombinant P peptide comprises the full-length phosphoprotein or at least the amino 1-50 of the phosphoprotein.

In particular, the recombinant P peptide is from 50 to 709 amino acids, preferably from 50 to 507 amino acids in length, more preferably from 50 to 300 amino acids in length. For example, the recombinant P peptide comprises at least the amino 1-50 of the phosphoprotein and has a length of 50, 60, 70, 80, 90, 100, 150, 200, 250, 300, 307, 350, 375, 400, 450, 500, 507, 550, 600, 650, 700 or 709 amino acids.

In the preferred embodiment, the N°P complexes are purified before adding RNA. In this case, the NC-like particles contain a chosen RNA. In this embodiment, the addition of RNA to the N°P complex is not achieved in cells since RNA is added to a solution of the purified N°P complex. This embodiment is appropriate for any application wherein the nature of RNA has to be controlled, including any method requiring NC-like particles with known RNA-content. Thus, the method of the invention will comprise a step of purification of N°P complexes for applications using analytical methods or where clearly defined NC-like particles are desired, as for instance for biotechnological applications.

Thus, in a preferred embodiment, the method for producing self-assembling paramyxoviral NC-like particles as described above is defined as a method wherein step (a) further comprises the purification of N°P complexes.

As used herein, the term "coexpression of N and P proteins" refers to the simultaneous expression of the two proteins in order to allow the formation of the N°P complex and consequently to avoid the formation of aggregates of insoluble N proteins. In the context of the present invention, the coexpression of N and P also encompasses situations where N is expressed in a medium where P is already present, provided that N will not form aggregates but N°P complexes with the available P proteins.

Concerning the length of the RNA molecule, it can vary, as the inventors have shown that both a short version of RNA with 6 nucleotides or a long molecule with 60 nucleotides allow the formation of the NC-like particles. Thus, the RNA length is not a determinant parameter as long as 6 nucleotides are present. A preferred RNA molecule corresponds to the 6 first nucleotides of the 5' end of the viral RNA. In a particular embodiment, the RNA molecule is not the native RNA of the virus. Further, in another preferred embodiment, the RNA terminates by a protecting group both on the 3' and 5' ends. In a more preferred embodiment, the RNA terminates by OH groups both on the 3' and 5' ends. Alternatively, the RNA molecule can for example be tagged at one extremity and bear an OH group at the other extremity. Appropriate tags are known by the skilled person in the art, as for example fluorescein.

In an embodiment, the invention relates to the method for producing self-assembling paramyxoviral NC-like particles as described above, wherein the RNA molecules comprises at least 6 nucleotides, preferably from 6 to 100 nucleotides, more preferably from 6 to 60 nucleotides.

For example, the RNA molecules has a length of 6, 7, 8, 9, 10, 20, 30, 40, 50, 60, 70, 80, 90 or 100 nucleotides.

In an embodiment, the method applies to the production of NC-like particles derived from measles virus. In this particular embodiment, N comprises at least the $N_{CORE}$ domain including the CTD arm and NTD arm, which corresponds to the folded domain of N and is represented by SEQ ID NO: 5. In other words, N comprises at least the amino acids 1-405 of SEQ ID NO: 4. Alternatively, N comprises the full-length N protein including the folded domain and the disordered C-terminal domain ($N_{TAIL}$) and is represented by SEQ ID NO: 4. Further, P comprises at least the minimal N-binding sequence, which is represented by SEQ ID NO: 2. In a particular embodiment, P consists of SEQ ID NO:2. In other words, P comprises at least the amino acids 1-50 of SEQ ID NO: 1.

Still regarding measles virus, in a particular embodiment, the RNA molecule comprises a sequence selected from the group comprising:
ACCAGACAAA GCUGGGAAUA GAAACUUCGU AUUUCAAAG UUUUCUUUAA UAUAUUGCAA (SEQ ID NO: 8), which corresponds to the first 60 nucleotides of the native RNA of the virus,
ACCAGACAAA (SEQ ID NO: 18), which corresponds to the first 10 nucleotides of the native RNA of the virus,
ACCAGA which corresponds to the first 6 nucleotides of the native RNA of the virus,
AAAAAAAAAA (SEQ ID NO: 19),
AAAAAA,
ACCUGA,
UCCAGA,
ACUAGA, and
AUCAGA.

In a further embodiment, the RNA molecule consists of a sequence selected from the group comprising: SEQ ID NO: 8, SEQ ID NO: 18, SEQ ID NO: 19, ACCAGA, AAAAAA, ACCUGA, UCCAGA, ACUAGA, and ACCAGA.

In an embodiment, the invention relates to the method for producing self-assembling paramyxoviral NC-like particles as described above, wherein the RNA molecules are not poly-U homopolymers, in particular not UUUUUU.

The production of NC-like particles from measles virus is illustrated in the experimental part. However, the method is directly applicable to the production of other Paramyxoviruses since viruses of this family are strongly related in terms of nucleoprotein/nucleocapsid sequence and architecture. However, it will be understood that other viruses being highly infectious pathogens, such as Nipah and Hendra viruses, the demonstration of the mechanism is safer with the measles virus.

Examples of other Paramyxoviruses are Nipah, Hendra, Mumps and human Parainfluenza viruses. Table 1 lists the paramyxoviruses for which the claimed method is directly applicable.

For Nipah, the claimed method can be carried out using the following sequences: For N peptide, the full-length protein corresponds to SEQ ID NO: 15. One can use either the amino acids 1-532 of the full-length protein or at least the amino acids 1-400 corresponding to the folded domain. For P peptide, one can use a peptide including at least the minimal N-binding domain which corresponds to residues 1-50 of the total P peptide represented by SEQ ID NO: 16. The peptide consisting of the residues 1-50 of the P peptide is represented by SEQ ID NO: 17.

Another object of the invention relates to a N°P complex comprising recombinant N and P peptides, wherein the N peptide comprises or consists of at least the $N_{CORE}$ domain including the CTD arm and NTD arm, and the P peptide comprises or consists of at least the N-binding domain.

In an embodiment, the invention relates to the N°P complex as described above, wherein the recombinant N peptide comprises the full-length nucleoprotein or at least the amino acids 1-400 corresponding to the $N_{CORE}$ domain of the nucleoprotein.

In particular, the recombinant N peptide is from 405 to 532 amino acids in length, preferably from 405 to 525 amino acids in length. For example, the recombinant N peptide has a length of 400, 410, 420, 430, 440, 450, 460, 470, 480, 490, 500, 510, 520, 525, 530 or 532 amino acids.

In an embodiment, the invention relates to the N°P complex as described above, wherein the recombinant P peptide comprises the full-length phosphoprotein or at least the amino 1-50 of the phosphoprotein.

In particular, the recombinant P peptide is from 50 to 709 amino acids in length, preferably from 50 to 507 amino acids in length. For example, the recombinant P peptide has a length of 50, 60, 70, 80, 90, 100, 150, 200, 250, 300, 350, 400, 450, 500, 507, 550, 600, 650, 700 or 709 amino acids.

In an embodiment, said N°P complex does not contain RNA.

In an embodiment, said N°P complex is purified.

Another object of the invention consists of a NC-like viral particle derived from a Paramyxovirus which comprises an RNA of interest, wherein the nature of RNA is controlled.

As used herein, the "control of the RNA" refers to the situation wherein the nature of the RNA that is embedded into the particles is known or predictable. It is indeed a specific characteristic of the invention to be able to control the nature of RNA that is embedded into NC particles. It is of great interest to be able to determine the conditions of entry of the RNA and thus the nature of the RNA. In particular, when the nature of the RNA is controlled, the sequence of the RNA embedded into the particles is known. The sequence of the RNA is chosen depending on the application of the NC-like particles. In order to obtain a homogenous population of NC-like particles with one type of RNA, the N°P complex can be purified to eliminate any contamination with cellular RNA, before adding the RNA of interest to a solution of N°P complex.

In an embodiment, the NC-like particles contain a synthetic RNA molecule.

In an embodiment, the NC-like particles contain only one given RNA molecule, in particular which is not viral RNA.

In an embodiment, the NC-like particles contain only one given RNA molecule, in particular which is not cellular RNA.

In an embodiment, the RNA is not a poly-U homopolymer, in particular is not UUUUUU.

In a preferred embodiment, the NC-like particles are obtainable by the method of production described above using recombinant N and P peptides and an RNA molecule of interest. Required for this assembly: (i) the N peptide comprising at least the $N_{CORE}$ domain including the CTD arm and NTD arm, (ii) a P peptide comprising at least the N-binding domain and (iii) an RNA molecule comprising at least 6 nucleotides.

The P peptide dissociates as the NC-like particle assembles, the latter comprises N peptide and RNA.

TABLE 1

Paramyxoviruses for which this method is directly applicable

| GENUS SPECIES | VIRUS (ABBREVIATION) |
|---|---|
| *Aquaparamyxovirus* | |
| Atlantic *salmon paramyxovirus* | Atlantic salmon paramyxovirus (AsaPV) |
| *Avulavirus Avian paramyxovirus 2* | avian paramyxovirus 2 (APMV-2) |

TABLE 1-continued

Paramyxoviruses for which this method is directly applicable

| GENUS SPECIES | VIRUS (ABBREVIATION) |
|---|---|
| *Avian paramyxovirus 3* | avian paramyxovirus 3 (APMV-3) |
| *Avian paramyxovirus 4* | avian paramyxovirus 4 (APMV-4) |
| *Avian paramyxovirus 5* | avian paramyxovirus 5 (APMV-5) |
| *Avian paramyxovirus 6* | avian paramyxovirus 6 (APMV-6) |
| *Avian paramyxovirus 7* | avian paramyxovirus 7 (APMV-7) |
| *Avian paramyxovirus 8* | avian paramyxovirus 8 (APMV-8) |
| *Avian paramyxovirus 9* | avian paramyxovirus 9 (APMV-9) |
| *Avian paramyxovirus 10* | avian paramyxovirus 10 (APMV-10) |
| *Avian paramyxovirus 11* | avian paramyxovirus 11 (APMV-11) |
| *Avian paramyxovirus 12* | avian paramyxovirus 12 (APMV-12) |
| *Newcastle disease virus* | avian paramyxovirus 1 (APMV-1) |
| *Ferlavirus* | |
| *Fer-de-Lance paramyxovirus* | Fer-de-Lance virus (FDLV) |
| *Henipavirus* | |
| *Cedar henipavirus* | Cedar virus (CedV) |
| *Ghanaian bat henipavirus* | Kumasi virus (KV) |
| *Hendra virus* | Hendra virus (HeV) |
| *Mojiang henipavirus* | Mo'jiang virus (MojV) |
| *Nipah virus* | Nipah virus (NiV) |
| *Morbillivirus* | |
| *Canine distemper virus* | canine distemper virus (CDV) |
| *Cetacean morbillivirus* | cetacean morbillivirus (CeMV) |
| *Feline morbillivirus* | feline morbillivirus (FeMV) |
| *Measles virus\** | measles virus (MeV) |
| *Peste-des-petits-ruminants virus* | peste-des-petits-ruminants virus (PPRV) |
| *Phocine distemper virus* | Phocine distemper virus (PDV) |
| *Rinderpest virus* | rinderpest virus (RPV) |
| *Respirovirus* | |
| *Bovine parainfluenza virus 3* | bovine parainfluenza virus 3 (BPIV-3) |
| *Human parainfluenza virus 1* | human parainfluenza virus 1 (HPIV-1) |
| *Human parainfluenza virus 3* | human parainfluenza virus 3 (HPIV-3) |
| *Porcine parainfluenza virus 1* | porcine parainfluenza virus 1 (PPIV-1) |
| *Sendai virus\** | Sendai virus (SeV) |
| *Rubulavirus* | |
| *Human parainfluenza virus 2* | human parainfluenza virus 2 (HPIV-2) |
| *Human parainfluenza virus 4* | human parainfluenza virus 4a (HPIV-4a) human parainfluenza virus 4b (HPIV-4b) |
| *Mapuera virus* | Mapuera virus (MapV) |
| *Mumps virus* | mumps virus (MuV) bat mumps virus (BMV) |
| *Parainfluenza virus 5* | parainfluenza virus 5 (PIV-5) |
| *Porcine rubulavirus* | La Piedad Michoaca'n Mexico virus (LPMV) |
| *Simian virus 41* | simian virus 41 (SV-41) |

Regarding the nature of the RNA molecule, it is contemplated to use any RNA of interest.

As used herein, the term "RNA of interest" refers to any RNA molecule of known sequence that allows the formation of the NC-like particles. Such RNA of interest can be chosen depending on the desired application of the NC-like particles. It can thus correspond to a viral RNA, from native or foreign virus, or to a non-viral RNA. The RNA of interest can be one type of molecule or be constituted by a mix of different types of RNA.

In an embodiment, only one specific RNA of interest is used.

In a particular embodiment, the invention consists of NC-like viral particles as previously defined wherein the N protein comprises a disordered N-terminal domain ($N_{TAIL}$) which is functionalized.

The functionalized group can be any biological molecule, any chemical compound or any group that provides a particular function to the particle. It can be one or more diversity elements to promote interactions with different protein targets in cells either for inducing a reaction or for tagging purposes. Examples of functionalized groups include ligands for a receptor, a dye compound, a photoreactive group for UV light-induced covalent cross-linking to interacting proteins, an alkyne handle for reporter tag conjugation to visualize and identify cross-linked proteins, a protein chimerically attached to $N_{TAIL}$ . . . . The skilled person in the art is familiar with collection of functionalized groups that can be added to a particular molecule or particles depending on the desired effect.

A functionalized particle is useful for numerous applications, in particular to target the particle to a desired organ or cellular type, for example to cancer cells, or to include domains of proteins attached to the flexible domain for the raising of antibodies for the development of vaccines.

It is indeed one of the aspects of the invention to be able to produce NC-like particles containing the same RNA molecule. This result could not have been achieved previously since NC particles obtained in cells, for example in *E. coli* or insects cells, have integrated the cellular RNA leading to a heterogeneous population of particles bearing each a particular RNA molecule. Providing NC-like particles with a defined RNA permits to better understand the replication cycle of Paramyxoviruses. It is indeed necessary to have a homogenous sample of particles to study the interaction between the RNA and the nucleocapsid for example by solid state NMR or high resolution cryo-electron microscopy. The present invention thus opens the way for new discovery regarding the mechanism of replication and transcription of these viruses.

Another object relates to a composition comprising NC-like viral particles as previously defined.

In a particular embodiment, said composition comprises a homogeneous population of particles bearing the same RNA.

Another object of the invention consists in the use of a NC-like viral particle as previously defined, as a medicament in the form of a drug or a vaccine.

Moreover, the ability to isolate integral N°P in a stable heterodimeric state that can be triggered to initiate NC-like assembly in the presence of RNA provides a powerful physico-chemical tool, not only to the study of the molecular basis of assembly, including the dynamics of NC-like assembly and possible dependence on RNA sequence and length, but more importantly to establish a tool for the development and testing of inhibitors of viral replication and transcription.

Another object of the invention consists of a method for identifying a compound able to inhibit the replication or transcription of a Paramyxovirus, wherein such compound is identified by its ability to abrogate the assembly of the NC-like particles.

Such screening method comprises the steps of:
a. Co-expressing recombinant N and P peptides in order to allow the formation of N°P complexes wherein:
   i. N peptide comprises at least the N-core domain including the CTD arm and NTD arm, and
   ii. P peptide comprises at least the N-binding domain;
b. Adding a compound to be tested;
c. Adding an RNA molecule wherein said the RNA molecule comprises at least 6 nucleotides and is preferably not a poly-U homopolymer;
d. Detecting the presence of NC-like particles in comparison with a control wherein no compound is present;
e. Identifying a compound able to inhibit the replication or transcription of a Paramyxovirus, where the assembly of the NC-like particles is inhibited in the presence of such compound, compared to control.

In a particular embodiment, the screening method consists in the method as defined above wherein step (a) further comprises the purification of N°P complexes. It can, however, also be performed on cell lysates containing N°P.

The quantification of assembled NC-like particles can be observed by any appropriate method including NMR or electron microscopy. Fluorescence based assays are appropriate for the development of rapid and efficient high-throughput assays.

For example, in a particular embodiment, dyes can be placed at the 3' terminus of an RNA molecule in a way that does not perturb assembly. This could be a 10-base RNA conjugated with a fluorescein derivative (FIG. 6). The assembly of the NC-like particles can be followed by fluorescence anisotropy. If a NC particle is formed, fluorescence anisotropy increases over time. The principle of this methodology is illustrated in FIG. 6. Such unambiguous read-out assays would be compatible with 96 (or higher) well plates for high-throughput screening of potential inhibitors of NC assembly, allowing for straightforward scaling to thousands or tens of thousands of compounds. FIG. 6 also shows the example of unsuccessful assembly as an unambiguous read out for capsid formation. In a fluorescence based assay, all samples would contain the same labelled RNAs. Only those wells that do not show an increase in anisotropy in the presence of a small molecule indicate successful NC formation inhibition and therefore a candidate for a drug.

In these kind of assays, the absence of NC-like particles or the decrease in quantity of NC-like particles produced directly results from the presence of a compound able to inhibit the assembly of the NC-like particles of Paramyxoviruses. As used herein, the "inhibition of the assembly of NC-like particles" may correspond to a total or partial inhibition.

The invention is further illustrated by the following examples that should not be considered as limiting the scope of the invention.

EXPERIMENTAL PART

Figure 1:
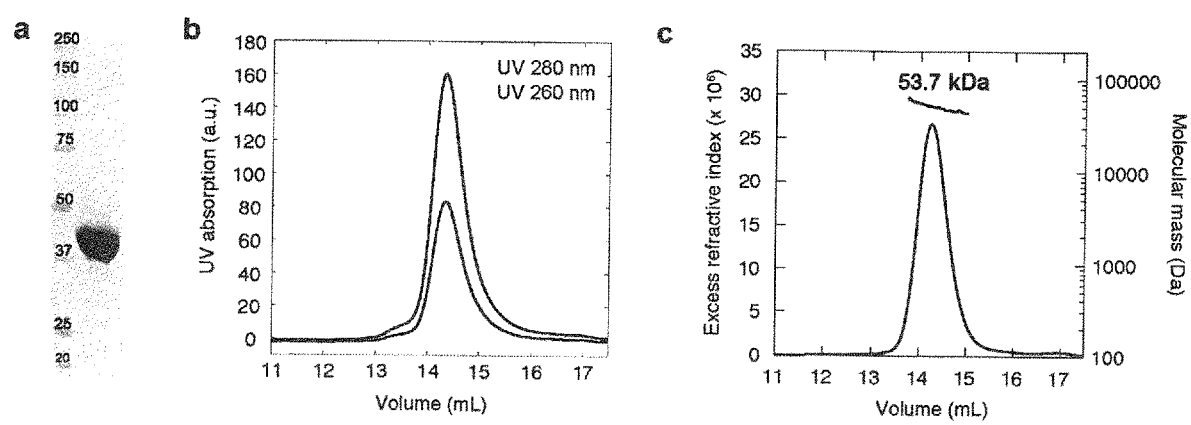
FIG. 1: Characterization of the $N_{2\text{-}405}°P_{1\text{-}50}$ complex. (a) SDS-PAGE gel (Coomassie blue staining) showing the purity of $N_{1\text{-}405}°P_{1\text{-}50}$ after cleavage by the TEV protease, Ni-affinity and size exclusion chromatography. $P_{1\text{-}50}$ being very small and weakly stained, only N is visible on the gel. Left lane shows molecular weight markers and numbers indicate the size of the respective bands (kDa). (b) Gel filtration profile of $N_{1\text{-}405}°P_{1\text{-}50}$ showing the UV absorption profiles at 260 and 280 nm demonstrating that the complex does not contain RNA. (c) Size exclusion chromatography combined with detection by multi-angle laser light scattering (MALLS) and refractometry of $N_{1\text{-}405}°P_{1\text{-}50}$ showing a mass of 53.7 kDa (expected mass for a heterodimeric complex: 52.6 kDa).
Figure 2:
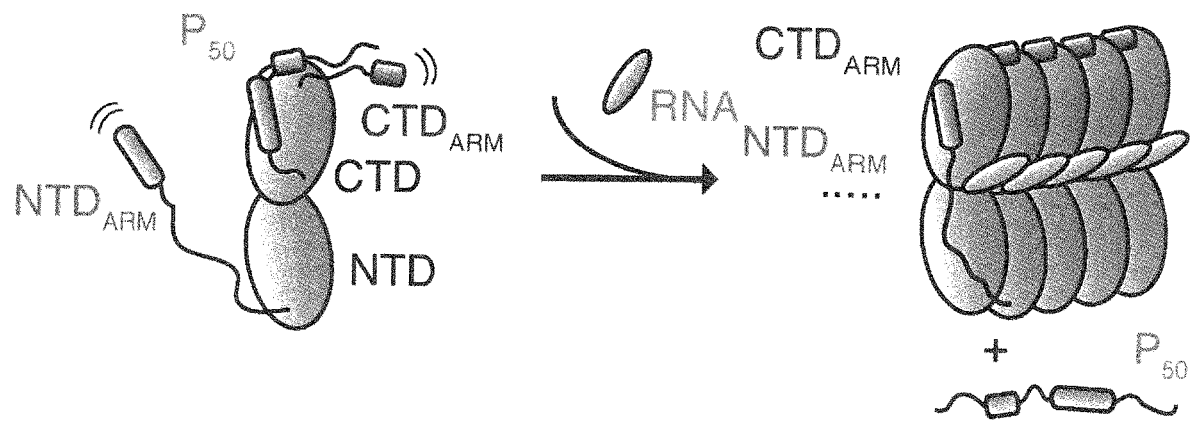
FIG. 2: Cartoon illustrating NMR signals that appear or disappear upon assembly of NC-like particles. In the Nip complex, both $NTD_{ARM}$ and $CTD_{ARM}$ of N are flexible, giving rise to observable backbone resonances in $^1H\text{-}^{15}N$ NMR spectra. $P_{1\text{-}50}$ is bound to N so that peaks are too weak to be observed. As N assembles, $NTD_{ARM}$ and $CTD_{ARM}$ stabilize the NC-like particles so that these peaks disappear, while resonances from $P_{1-50}$ grow as more N proteins associate.

Example 1: Constructs for Expression of P Peptide

Materials and Methods

The measles virus (Edmonston strain; UniProt Q83623) phosphoprotein (also called P) used in this work corresponds to SEQ ID NO: 1. The first 50 amino acids of the $P_{1-50}$ corresponds to SEQ ID NO 2.

$P_{1-100}$: DNA of first 100 amino acids of measles virus P protein were cloned into a pET41c (+) vector between NdeI and XhoI sites resulting in a C-terminal His-tagged construct.

Escherichia coli Rosetta™ (λDE3)/pRARE strain (Novagen) were used for the production of $P_{1-100}$. The protein was purified by nickel resin chromatography, followed by size exclusion chromatography.

Results

NMR backbone resonances from the first 300 amino acids of P were assigned using standard three-dimensional heteronuclear NMR. The majority of the chain exhibits conformational propensities that are characteristic of an unfolded chain, with the exception of the first 40 amino acids, that shows a slightly elevated additional α-helical propensity. Although sequence homology is negligible, this N-terminal localization coincides with the position of a P peptide that was recently co-crystallised with an N and C-terminal deleted N protein from Nipah virus by the inventors.[8] This region was targeted as the putative N-binding site. The inventors therefore co-expressed MeV $P_{1-100}$ with N, resulting in a soluble and stable complex $N_{CORE}°P_{1-100}$. The binding site was then delineated more precisely by titrating $^{15}N/^{13}C$ labeled $P_{1-150}$ into $N_{CORE}°P_{1-00}$, showing localized exchange in the region comprising residues 1-50.

This entire procedure resulted in identification of the minimal P peptide ($P_{1-50}$ of SEQ ID NO: 2) required to form the complex.

Example 2: In Vitro Co-Expression of N and P Proteins as a Heterodimeric Complex Materials and Methods The measles virus nucleoprotein (also called N) (Edmonston strain; UniProt 089933) used in this work comprises 525 amino acids and corresponds to SEQ ID NO: 4.

Constructs

The first 50 amino acids of measles virus phosphoprotein (Edmonston strain; UniProt Q83623) in fusion with the 525 or 405 amino acids of measles virus nucleoprotein (Edmonston strain; UniProt Q89933) with a TEV protease cleavage site inserted between the two (ENLYFQG) were cloned into a pET41c (+) vector following a two step PCR reaction:

Step 1: The PCR products for P peptide and N peptide were obtained separately using the following amplification primers.

```
For P1-50:
Forward:
                             (SEQ ID NO: 9)
5'-GGAATTCCATATGGCAGAGGAGCAGGCACGCCATGTCA-3'

Reverse:
                             (SEQ ID NO: 10)
5'-CATGCCCTGAAAATACAGGTTTTCGCAGGTGGCTCGCTCC-3'

For N1-525:
Forward:
                             (SEQ ID NO: 11)
5'-GCCACCTGCGAAAACCTGTATTTTCAGGGCATGGCCACACTTTTAA
G-3'

Reverse:
                             (SEQ ID NO: 12)
5'-CCGGTCGACGTCTAGAAGATTTCTGTCATTGTACACTATAGGGGT
G-3'

For N1-405:
Forward primer identical to SEQ ID NO: 11.

Reverse N:
                             (SEQ ID NO: 13)
5'-GCGTCGACCTTGTTCTCAGTAGTATGCATTGCAATCTCTG-3'
```

The resulting PCR products were purified on an agarose gel.

Step 2: The purified PCR products obtained at step 1 were mixed in a stoichiometric ratio (about 10 ng of N with about 50 ng of P), heated to 95° C. during 5 min and cooled down to 20° C. during 30 min. The mix was supplemented with 2× MasterMix (Fermentas™) and submitted to 5 cycles: 95° C. 45 s 72° C. 1.5 min.

The combined product was then purified (PCR purification kit—Qiagen™) and PCR amplified with the external primers used previously:

Forward: 5'-(SEQ ID NO: 9) and Reverse: 5'-(SEQ ID NO: 12) to yield $N_{1-525}°P_{1-50}$. For $N_{1-405}°P_{1-50}$, SEQ ID NO: 12 was replaced by SEQ ID NO: 13 in the final amplification step.

The resulting products were purified on an agarose gel, digested with NdeI and SalI enzymes and inserted between the NdeI and XhoI sites of a digested pET41c (+) plasmid.

Expression and Purification of N°P

*Escherichia coil* Rosetta™ (λDE3)/pRARE strain (Novagen) were also used for the production of $N_{1-525}°P_{1-50}$ and $N_{1-405}°P_{1-50}$.

For protein expression, cultures were grown at 37° C. in LB until OD600=0.6 was observed, then the temperature was lowered to 20° C. and expression induced with 1 mM IPTG. Cells were harvested after 12-14 hours. For expression of labelled protein, initial 4 liter cultures were grown in LB medium and the cells transferred into 1 liter M9 medium at an OD600 of 0.6. The cells were then grown for an additional 1 hour at 20° C. before induction.

For protein purification, cells were lysed in 20 mM Tris pH 8, 150 mM NaCl, 1 tablet Roche complete EDTA-free protease inhibitors, 1 spatula tip of lysozyme by sonication. Cell debris was harvested by centrifugation and supernatant loaded on Ni-beads (His-select, Sigma Aldrich™). The flow through was discarded and beads were washed with 20 mM Tris pH 8, 150 mM NaCl, 8 mM imidazole. The protein was eluted from the beads in 20 mM Tris pH 8, 150 mM NaCl, 400 mM imidazol. TEV cleavage was set up overnight and at the same time the protein was dialyzed against 20 mM Tris pH 8, 150 mM NaCl, 5 mM beta-mercaptoethanol (BME). The protein was then purified by gel filtration (Superdex 200 column, GE Healthcare™) equilibrated with either the same buffer or the NMR buffer (50 mM phosphate pH 7, 150 mM NaCl, 5 mM BME).

Cleavage with TEV gave the following proteins in complex N°P for $N_{1-525}°P_{1-50}$:

$P_{1-50}$ with a TEV peptide amino acid sequence is represented by SEQ ID NO: 3.

$N_{1-525}$ with an Histidine tag is represented by SEQ ID NO: 6.

And for $N_{1-405}°P_{1-50}$, cleavage with TEV gave the following proteins:

$P_{1-50}$ with a TEV peptide amino acid sequence is represented by SEQ ID NO: 3.

$N_{1-405}$ with an Histidine tag is represented by SEQ ID NO: 7.

Results

Coexpression of constructs containing the $P_{1-50}$ peptide and either full length N ($N_{1-525}$) or the folded domain of N ($N_{1-405}$), separated by a TEV cleavage site resulted in high yield, heterodimeric, soluble and stable N°P complex. Small angle X-ray scattering and multi-angle laser light scattering (MALLS) of $N_{1-405}°P_{1-50}$ or $N_{1-525}°P_{1-50}$ demonstrate that both constructs contain a heterodimer of monomers of $P_{1-50}$ and $N_{1-525}$ or $N_{1-405}$ (FIG. 1).

This result demonstrates that the inventors have successfully produced a heterodimeric, soluble and stable N°P complex. It constitutes a rational basis for the design of a tool with which to mimic the initial steps of the viral replication cycle, by stabilizing for the first time the chaperoned state of N that precedes NC formation in solution, while respecting the integral native sequence of N. In order to demonstrate the potential of such a tool, the inventors have further investigated the interaction of this complex with RNA as described thereafter.

Example 3: Production of NC-Like Particles

Materials and Methods

RNA molecules added to the N°P complex

RNA was added to the N°P complexes by titrating a solution of the two following particular RNA sequence:

6 nucleotide long RNA: 5' OH-ACCAGA-OH 3' ($RNA_6$)
60 nucleotide long RNA:

```
5' OH-ACCAGACAAAGCUGGGAAUAGAAACUUCGUAUUUUCAAGUUUUC
UUUAAUAUAUUGCAA-OH 3' (naked RNA corresponds to
SEQ ID NO: 8)
```

10 nucleotide long RNA containing a fluorescein attached at its 3'end: 5' OH-ACCAGACAAA-FAM (naked RNA corresponds to SEQ ID NO: 14).

NC-like particles can then be further purified using the methods described in reference 4.

NMR Spectroscopy

Figure 3:
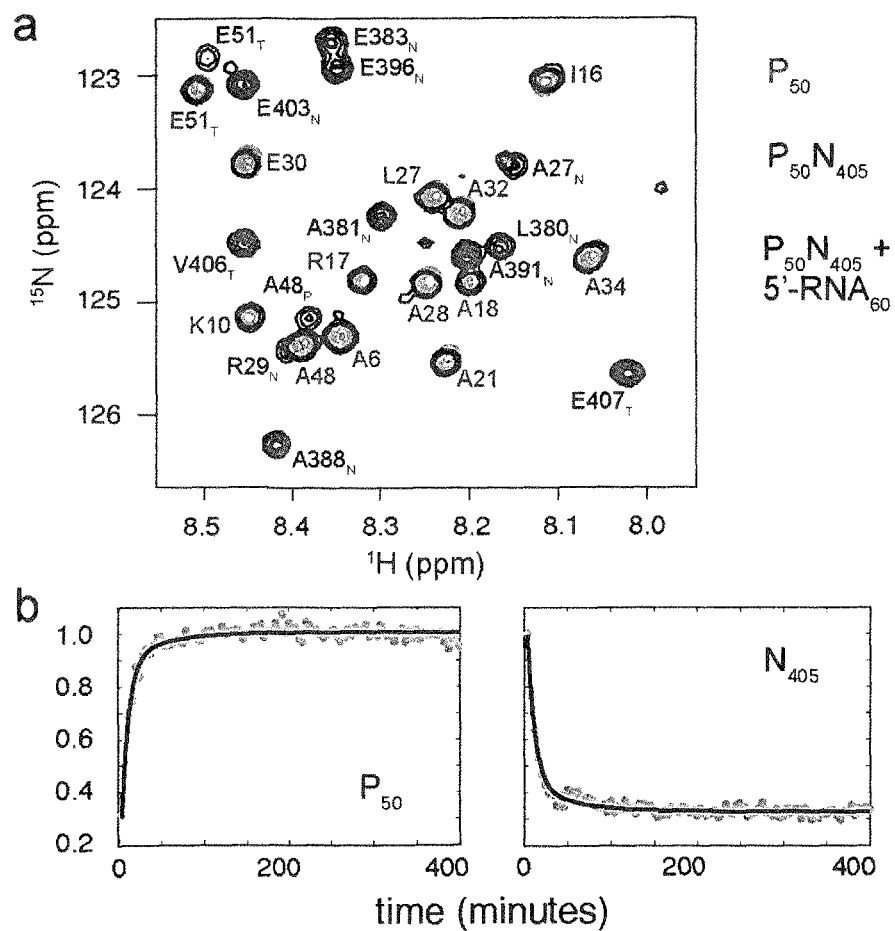
FIG. 3: a) Part of the $^1H$-$^{15}N$ spectrum of $N_{1-405}°P_{1-50}$, $P_{1-50}$ and $N_{1-405}°P_{1-50}$ after incubation with 5'-$RNA_{60}$ for 24 hours at 25° C. Assignments are shown for the $N_{1-405}°P_{1-50}$ and $P_{1-50}$ resonances. Subscript T refers to residues associated with cleavage or affinity tags. b) Assembly of NC-like particles from $N_{1-405}°P_{1-50}$ with 5'-$RNA_6$ was initiated from 209 µM $N_{1-405}°P_{1-50}$, adding 5'-$RNA_6$ to 471 µM. Circles: intensities measured in SOFAST HMQC NMR spectra and summed over appearing $P_{1-50}$ (left) or disappearing $N_{1-405}$ (right) resonances ($P_{1-50}$: 4, 5, 6, 22, 25, 38, $N_{1-405}$: 28, 385, 386, 387, 388, 389, 404, 405), lines: simultaneous fit to a double-exponential with common assembly rates.
Figure 4:
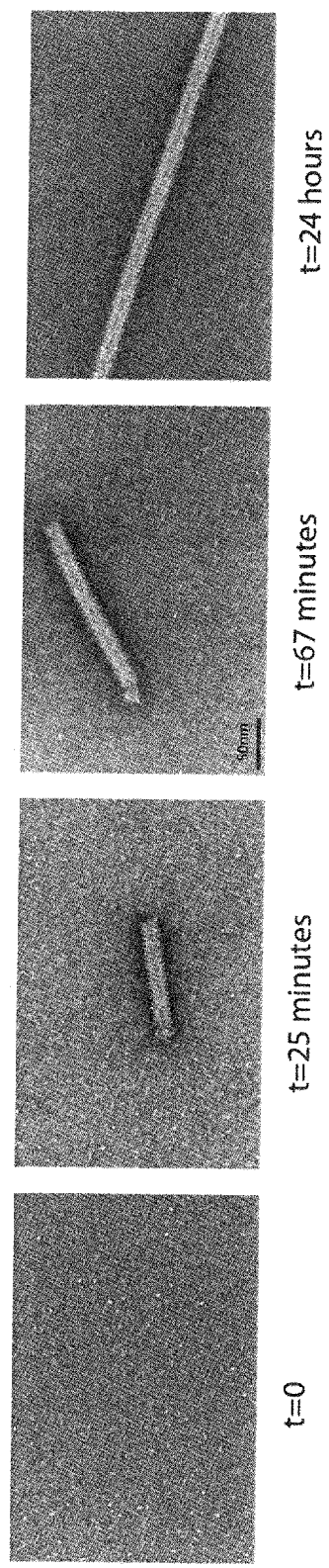
FIG. 4: Following NC assembly by electron microscopy. Negative staining electron micrographs of $N_{1-405}°P_{1-50}$ in the presence of a 6 nucleotide RNA from the 5' end of the measles virus genome. Images were taken at different time points following mixing of the two components in vitro.
Figure 5:
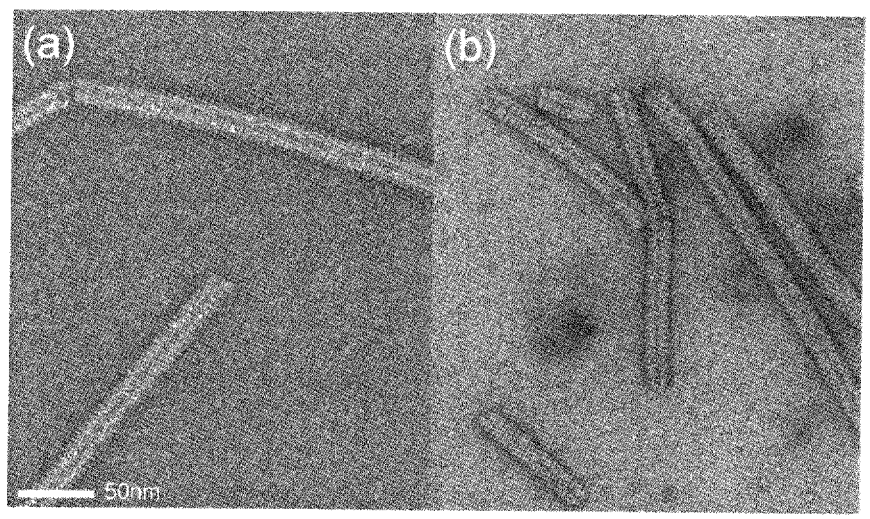
FIG. 5: NC assembly in vitro reproduces NC assembly in vivo. (A) Negative staining electron micrograph of $N_{1-405}°P_{1-50}$ in the presence of a 6 nucleotide RNA from the 5' end of the measles virus genome (negative staining). (B) Electron micrographs of trypsin digested nucleocapsids purified from E. coli genetically engineered to overexpress N protein.
Figure 6:
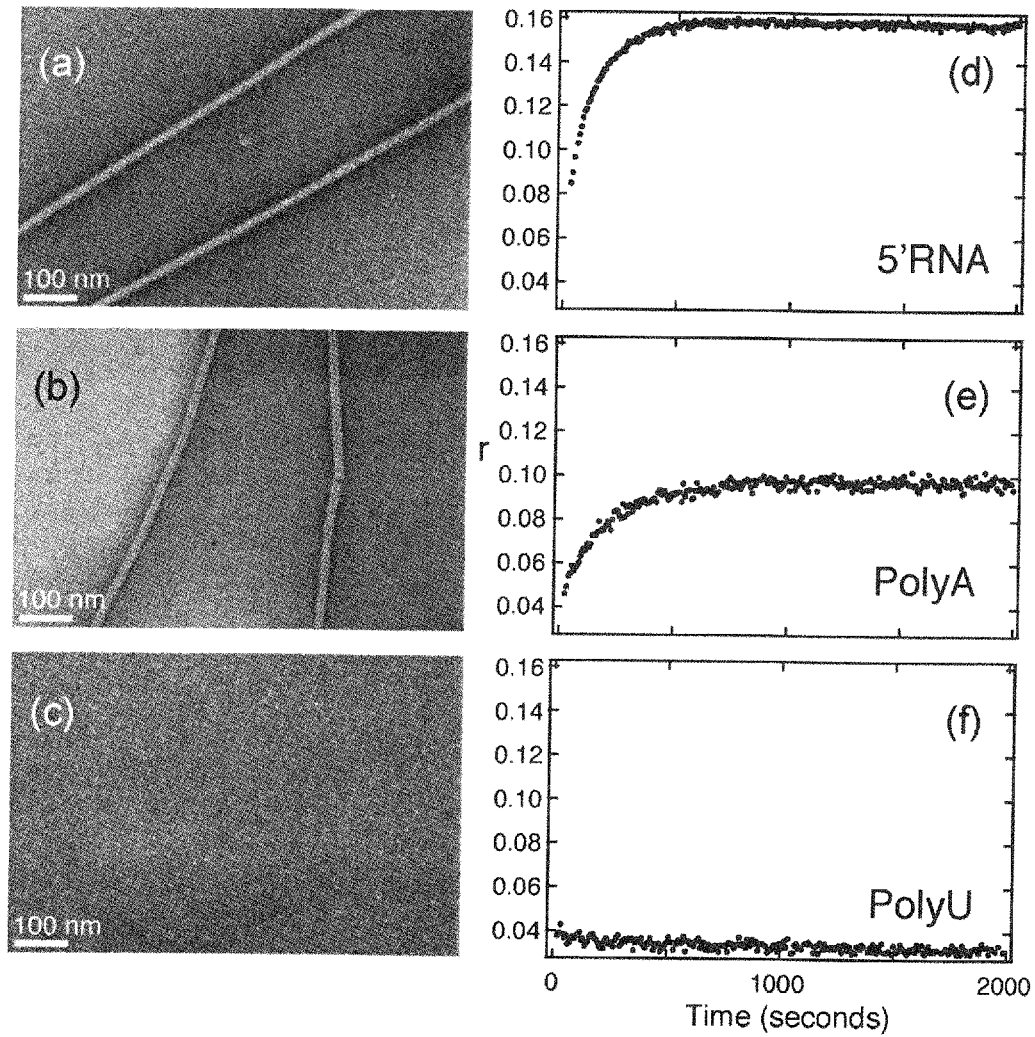
FIG. 6: Dependence of NC-like particles assembly on RNA sequence. (a-c) $N_{1-405}°P_{1-50}$ was incubated with different RNAs for 24 hours at room temperature and visualized by negative stain electron microscopy. Assembly of NC-like particles is observed for a) 5'-$RNA_6$, b) polyA-$RNA_6$, while no assembly is observed for c) polyU-$RNA_6$; (d-f) Fluorescence anisotropy during 2000 seconds after addition of 500 nM for d) 5'-$RNA_{10}$-FAM (ACCAGACAAA, SEQ ID NO: 18), e) polyA$_{10}$-FAM (AAAAAAAAAA, SEQ ID NO: 19) and f) polyU$_{10}$-FAM (UUUUUUUUUU, SEQ ID NO: 20) to 23 µM $N_{1-405}°P_{1-50}$.
Figure 7:
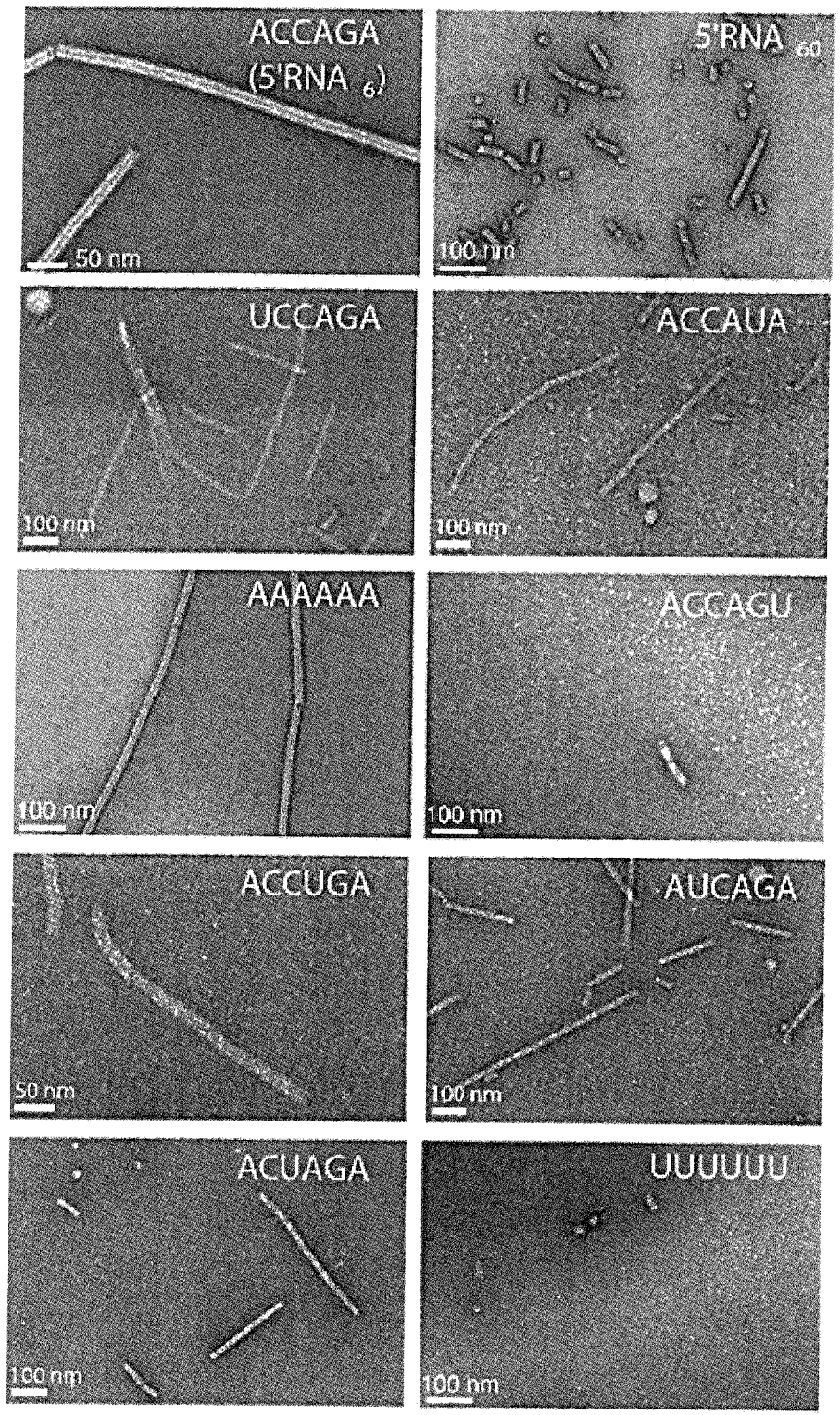
FIG. 7. NC assembly in vitro. $N_{1-405}°P_{1-50}$ was incubated with different RNAs for >12 hours at room temperature and visualized by electron microscopy. Assembly of NC-like particles is observed for 5'-$RNA_6$ ACCAGA, 5'-$RNA_{60}$ (SEQ ID NO: 8), AAAAAA, ACCUGA, UCCAGA, ACUAGA and AUCAGA while no assembly is observed for UUUUUU.

The assembly of NC-like particles was followed by real-time NMR using a series of SOFAST $^1H$-$^{15}N$ HMQC experiments using a sample of 200 μM N°P complex ($N_{1-405}°P_{1-50}$ or $N_{1-525}°P_{1-50}$) The formation of NC-like particles was initiated by addition of $RNA_6$ or $RNA_{60}$ (SEQ ID NO: 8) reaching a total concentration of 20 μM ($RNA_{60}$) or 150 μM ($RNA_6$). A series of SOFAST HMQC experiments were recorded with 100 complex points in the indirect dimension, a 200 ms recycling delay and 4 transients providing a time resolution of 4 minutes. The spectra were recorded on a Bruker spectrometer operating at a $^1H$ frequency of 950 MHz at 25° C. in a buffer consisting of 50 mM phosphate buffer, 150 mM NaCl, 5 mM BME at pH 7.0. In addition, two additional SOFAST HMQC experiments were recorded in the absence of RNA and at the end of the time course (after 24 h) with 256 complex points in the indirect dimension and 16 transients (FIG. 3A).

Electron Microscopy

The formation of NC-like particles was followed by negative staining electron microscopy. Initially, a control measurement was performed of the $N_{1-405}°P_{1-50}$ complex in the absence of $RNA_6$ showing no formation of NC-like particles. The $N_{1-405}°P_{1-50}$ was then mixed with RNA6 and the sample was visualized by electron microscopy. The sample contained 20 μM of $N_{1-405}°P_{1-50}$ and 50 μM of $RNA_6$ in the same buffer as used for the NMR experiments (see above).

Fluorescence Spectroscopy $N_{1-405}°P_{1-50}$ or $N_{1-525}°P_{1-50}$ was diluted to the desired concentration into 50 mM Na-phosphate pH 7, 150 mM NaCl, 5 mM β-mercaptoethanol (β ME) directly into the fluorescence cuvette. $RNA_{10}$-FAM (SEQ ID NO: 14) was added to N°P immediately to a final concentration of 500 nM prior to kinetics acquisition, mixed quickly through pipetting and fluorescence kinetics were recorded at an emission wavelength of 520 nm upon excitation with 470 nm light. Parallel and perpendicular polarization directions were recorded alternatingly and used pairwise to calculate the fluorescence anisotropy r $$r = \frac{I_\parallel - GI_\perp}{I_\parallel + 2GI_\perp}$$

with the G-factor correcting for detection differences between parallel ($I_\parallel$) and perpendicular ($I_\perp$) polarized fluorescence light. G was determined on a daily basis according to standard protocols, and remained stable between days. Fluorescence spectra were recorded at the end of the assembly kinetics with an excitation wavelength of 460 nm and an emission range of 470-650 nm.

Protocol for Application to Other Paramyxoviruses

For Nipah, the claimed method can be carried out using the following sequences:

For N peptide, the full-length protein (1-532) corresponds to SEQ ID NO: 15.

One could use either the amino acids 1-532 of the full-length protein or the amino acids 1-400 corresponding to the folded domain. For P peptide, one could use a peptide including the minimal N-binding domain which corresponds to residues 1-50 of the total P peptide represented by SEQ ID NO: 16. The peptide consisting of the residues 1-50 of the P peptide is represented by SEQ ID NO: 17.

Results

Analysis by NMR Spectroscopy

Using NMR spectroscopy, the inventors were able to follow the evolution in real time of the NMR spectra as the $P_{1-50}$ peptide is released from the N°P complex and the NC-like particles are formed. This result is observed either by following the increasing intensity of peaks corresponding to the $P_{1-50}$ peptide, or by observing the reduction in intensity of peaks associated with the N- and C-terminal tails of the N protein that become immobile upon assembly of the NC-like particles, according to the mechanism illustrated in FIG. 2. A time trace of the formation of the NC-like particles was obtained by extracting the NMR signal intensities from each of the SOFAST HMQC spectra and plotted as function of time after addition of the RNA (FIGS. 3B and 3C). After a rapid growth phase (<30 minutes) the assembly process is nearly complete within approximately 400 minutes. This result demonstrates that NMR allows to follow the formation of NC-like particles in vitro using only short RNA molecules and the N°P complex.

Analysis by Electron Microscopy

Electron microscopy was carried out on samples immobilized at increasing times after addition of small (6 or 60 nucleotides in length) RNA molecules.

The $N_{1-405}$°$P_{1-50}$ mixed with $RNA_6$ was visualized by electron microscopy after 25 minutes and 67 minutes as well as after 24 hours showing the presence of NC-like particles of increasing lengths (FIG. 4). These results confirmed the NMR-detected time course. Remarkably, even in the presence of relatively short RNA, NC-like particles were formed whose electron micrographs were indistinguishable from NC-like particles purified from *E. coli* (FIG. 5). These results demonstrate that EM allows to follow the formation of NC-like particles in vitro using only short RNA molecules and the NT complex.

Analysis by Fluorescence Spectroscopy

Fluorescence anisotropy also reports on assembly, using fluorescein labeled RNA (SEQ ID NO: 14). Fluorescein attached to the RNA alone undergoes fast rotation, and exhibits a small fluorescence anisotropy when the RNA is unbound. Upon binding to N, NC-like particle formation and subsequent elongation, its rotational freedom is significantly hindered, and fluorescence anisotropy increases gradually, giving rise to anisotropy curves that describe the NC-like particle assembly.

Different RNA sequences were tested for their ability to facilitate NC-like particle assembly in vitro from $P_{1-50}$ $N_{1-405}$. Homopolymers comprising purines or pyrimidines alone, UUUUUU (polyU-$RNA_6$), AAAAAA (polyA-$RNA_6$) were compared, as well as genomic 5'-$RNA_6$. Remarkably, efficiency of assembly is sequence-dependent (FIG. 6). No assembly is observed for the polyU-$RNA_6$ samples (FIG. 6*c, f*), while regular NC-like particles are obtained for 5'-$RNA_6$ and polyA-$RNA_6$ (FIGS. 6*a, d* and 6b, e respectively) with lengths reaching 1-2 μm. This differential ability to form NC-like particles was verified by NMR (data not shown). With this respect, the inventors have also noted that the 5' sequences of both genome and anti-genome of paramyxovirinae shows strong conservation of ACCA in the first four nucleotides, followed by positions 5 and 6 occupied mainly by A/G. Indeed, the 5' sequence of the measles genome leads to formation of NCs with high efficiency.

CONCLUSION

It is therefore possible, using the described method, to both detect and monitor NC assembly in vitro from recombinantly-expressed protein and RNA alone, in the absence of other viral or cellular partners.

REFERENCES (1) Curran, J., and Kolakofsky, D. (1999) Replication of paramyxoviruses. *Adv. Virus Res.* 54, 403-422.

(2) Communie, G., Ruigrok, R. W., Jensen, M. R., and Blackledge, M. (2014) Intrinsically disordered proteins implicated in paramyxoviral replication machinery. *Curr. Opin. Ora 5C,* 72-81.

(3) Bhella, D., Ralph, A., Murphy, L. B., and Yea, R. P. (2002) Significant differences in nucleocapsid morphology within the Paramyxoviridae. *J. Gen. Virol.* 83, 1831-1839.

(4) Schoehn, G., Mavrakis, M., Albertini, A., Wade, R., Hoenger, A., and Ruigrok, R. W. H. (2004) The 12 A structure of trypsin-treated measles virus N-RNA. *J. Mol. Biol.* 339, 301-312.

(5) Loney, C., Mottet-Osman, G., Roux, L., and Bhella, D. (2009) Paramyxovirus ultrastructure and genome packaging: cryo-electron tomography of sendai virus. *J. Viral.* 83, 8191-8197.

(6) Desfosses, A., Goret, G., Farias Estrozi, L., Ruigrok, R. W. H., and Gutsche, I. (2011) Nucleoprotein-RNA orientation in the measles virus nucleocapsid by three-dimensional electron microscopy. *J. Virol.* 85, 1391-1395.

(7) Gutsche, I., Desfosses, A., Effantin, G., Ling, W. L., Haupt, M., Ruigrok, R. W. H., Sachse, C., and Schoehn, G. (2015) Near-atomic cryo-EM structure of the helical measles virus nucleocapsid. *Science,* 348, 6235, 704-707.

(8) Yabukarski, F., Lawrence, P., Tarbouriech, N., Bourhis, J.-M., Delaforge, E., Jensen, M. R., Ruigrok, R. W. H., Blackledge, M., Volchkov, V., and Jamin, M. (2014) Structure of Nipah virus unassembled nucleoprotein in complex with its viral chaperone. *Nat. Struct. Mol. Biol.* 21, 754-759.

(9) Jensen, M. R., Communie, G., Ribeiro, E. A., Jr, Martinez, N., Desfosses, A., Salmon, L., Mollica, L., Gabel, F., Jamin, M., Longhi, S., Ruigrok, R. W. H., and Blackledge, M. (2011) Intrinsic disorder in measles virus nucleocapsids. *Proc. Natl. Acad. Sci. U.S.A* 108, 9839-9844.

(10) Communie, G., Habchi, J., Yabukarski, F., Blocquel, D., Schneider, R., Tarbouriech, N., Papageorgiou, N., Ruigrok, R. W. H., Jamin, M., Jensen, M. R., Longhi, S., and Blackledge, M. (2013) Atomic resolution description of the interaction between the nucleoprotein and phosphoprotein of Hendra virus. *PLoS Pathog.* 9, e1003631.

(11) Spehner, D., Drillien, R., and Howley, P. M. (1997) The assembly of the measles virus nucleoprotein into nucleocapsid-like particles is modulated by the phosphoprotein. *Virology* 232(2), 260-268.

(12) Cox, R., Green, T. J., Qiu, S., Kang, J., Tsao, J., Prevelige, P. E., He, B., and Luo M. (2009) Characterization of a mumps virus nucleocapsidlike particle. *J Viral.* 83, 11402-11406

(13) Juozapaitis, M., Slibinskas, R., Staniulis, 0.1., Sakaguchi, T., Sasnauskas, K. (2005) Generation of Sendai virus nucleocapsid-like particles in yeast. *Virus Res.* 108(1-2), 221-224.

The invention claimed is:

1. A method for producing self-assembling paramyxoviral nucleocapsid-like particles comprising the steps of:
   a. co-expressing recombinant nucleoprotein (N) and phosphoprotein (P) proteins in order to allow the formation of N°P complexes wherein:
      i. the recombinant N protein comprises an $N_{CORE}$ domain including a C-terminal domain (CTD) arm and an N-terminal domain (NTD) arm, and
      ii. the recombinant P protein comprises an N-binding domain;

b. purifying N°P complexes, the purified N°P complexes comprising recombinant N and P proteins only and being RNA-free;

c. adding RNA molecules of interest to the purified N°P complexes, wherein the RNA molecules of interest comprise at least 6 nucleotides and are not poly-U homopolymers; and d. recovering the resulting nucleocapsid-like particles.

2. The method of claim 1 wherein the recombinant N and P proteins correspond to proteins from measles virus, wherein recombinant N protein corresponds to SEQ ID NO.4 or SEQ ID NO.5 and recombinant P protein comprises SEQ ID NO.2.

3. A paramyxoviral nucleocapsid-like viral particle produced by the method of claim 1, wherein said nucleocapsid-like viral particle comprises only one specific type of RNA molecule of interest, and wherein said RNA molecule of interest is a synthetic RNA molecule.

4. The nucleocapsid-like viral particle of claim 3 wherein the N protein comprises a disordered C-terminal domain which is functionalized with a group selected from a ligand for a receptor, a dye compound, a photoreactive group for UV light-induced covalent cross-linking to interacting proteins, an alkyne handle for reporter tag conjugation to visualize and identify cross-linked proteins, and a protein chimerically attached to $N_{TAIL}$.

5. A method for identifying a compound able to inhibit the replication or transcription of a Paramyxovirus, wherein such compound is identified by its ability to abrogate the assembly of the nucleocapsid-like particles according to claim 1.

6. A method for identifying a compound able to inhibit the replication or transcription of a Paramyxovirus comprising the steps of:

a. co-expressing recombinant N and P proteins in order to allow the formation of N°P complex wherein:

i. the recombinant N protein comprises an N-core domain including a CTD arm and an NTD arm, and ii. the recombinant P protein comprises an N-binding domain;

b. purifying N°P complexes, the purified N°P complex comprising recombinant N and P proteins only and being RNA-free;

c. adding a compound to be tested;

d. adding a RNA molecule wherein said RNA molecule comprises at least 6 nucleotides and is not a poly-U homopolymer;

e. detecting the presence of nucleocapsid-like particles in comparison with a control wherein no compound is present; and f. identifying a compound able to inhibit the replication or transcription of a Paramyxovirus, where the assembly of nucleocapsid-like particles is inhibited in the presence of such compound, compared to control.

7. The method of claim 6 wherein identifying the compound in step (f) is performed using a fluorescent read-out assay, in particular a high-throughput assay.

* * * * *

UNITED STATES PATENT AND TRADEMARK OFFICE
CERTIFICATE OF CORRECTION

| | | |
|---|---|---|
| PATENT NO. | : 11,319,350 B2 | Page 1 of 1 |
| APPLICATION NO. | : 16/306843 | |
| DATED | : May 3, 2022 | |
| INVENTOR(S) | : M. Blackledge et al. | |

It is certified that error appears in the above-identified patent and that said Letters Patent is hereby corrected as shown below:

On the Title Page

Item (71) Applicants:
Please add -- CENTRE NATIONAL DE LA RECHERCHE SCIENTIFIQUE, Paris (FR) --.

Signed and Sealed this
Twenty-first Day of March, 2023

Katherine Kelly Vidal
*Director of the United States Patent and Trademark Office*